(12) United States Patent
Teßarek et al.

(10) Patent No.: US 12,226,305 B2
(45) Date of Patent: Feb. 18, 2025

(54) MULTILUMEN IMPLANT (71) Applicant: Stental GmbH, Lörrach (DE)

(72) Inventors: Jörg Teßarek, Lingen (DE); Milisav Obradovic, Lörrach (DE)

(73) Assignee: Stental GmbH, Loerrach (DE)

( * ) Notice: Subject to any disclaimer, the term of this patent is extended or adjusted under 35 U.S.C. 154(b) by 539 days.

(21) Appl. No.: 16/461,922

(22) PCT Filed: Nov. 14, 2017

(86) PCT No.: PCT/EP2017/079148
§ 371 (c)(1),
(2) Date: May 17, 2019

(87) PCT Pub. No.: WO2018/091442
PCT Pub. Date: May 24, 2018

(65) Prior Publication Data
US 2019/0321161 A1  Oct. 24, 2019

(30) Foreign Application Priority Data
Nov. 18, 2016 (DE) ...................... 10 2016 122 223.2

(51) Int. Cl.
*A61F 2/07* (2013.01)
*A61F 2/06* (2013.01)
*A61F 2/82* (2013.01)
*A61F 2/844* (2013.01)
*A61M 25/00* (2006.01)

(52) U.S. Cl.
CPC .......... *A61F 2/07* (2013.01); *A61M 25/0026* (2013.01); *A61F 2002/068* (2013.01); *A61F 2002/077* (2013.01); *A61F 2002/823* (2013.01); *A61F 2/844* (2013.01)

(58) Field of Classification Search
CPC .......... A61F 2002/065; A61F 2002/067; A61F 2002/068; A61F 2/954; A61F 2/856; A61F 2/852
See application file for complete search history.

(56) References Cited

U.S. PATENT DOCUMENTS

| 2003/0065385 | A1 | 4/2003 | Weadock |
| 2003/0176911 | A1 | 9/2003 | Iancea et al. |
| 2005/0021132 | A1 | 1/2005 | Bolduc et al. |
| 2009/0099649 | A1* | 4/2009 | Chobotov ............... A61F 2/966 623/1.36 |
| 2011/0276062 | A1* | 11/2011 | Bolduc .............. A61B 17/3468 606/139 |

(Continued)

FOREIGN PATENT DOCUMENTS

| DE | 102012100754 A1 | 8/2013 |
| EP | 2081515 B1 | 10/2015 |

(Continued)

*Primary Examiner* — Sarah A Long
*Assistant Examiner* — Raihan R Khandker
(74) *Attorney, Agent, or Firm* — Brooks Kushman P.C.

(57) ABSTRACT

The invention relates to a multilumen implant for the application in human and animal bodies, comprising a substantially tubular element (1) that divides into a proximal (2) and a distal section (3), and at least one stent (8) for the fixation of the proximal section in a target vessel, wherein the tubular element (1) is designed to branch in the distal section (3) into at least two lumens (4, 5).

15 Claims, 10 Drawing Sheets (56) References Cited

U.S. PATENT DOCUMENTS

| | | |
|---|---|---|
| 2013/0138202 A1 | 5/2013 | Paul et al. |
| 2014/0074218 A1 | 3/2014 | Leopold et al. |
| 2015/0305852 A1 | 10/2015 | Hartley et al. |
| 2016/0081787 A1 | 3/2016 | Parodi et al. |
| 2016/0184078 A1 | 6/2016 | Choubey et al. |
| 2016/0324626 A1 | 11/2016 | Kelly |

FOREIGN PATENT DOCUMENTS

| | | |
|---|---|---|
| EP | 2749251 B1 | 7/2016 |
| WO | WO98/44873 A1 | 10/1998 |
| WO | WO2012/084202 A2 | 6/2012 |
| WO | WO2014/197743 A1 | 12/2014 |

\* cited by examiner

MULTILUMEN IMPLANT

The invention relates to a multilumen implant for application in human and animal vascular systems comprising an essentially tubular element divided into a proximal and a distal section, and at least one stent for fixing the proximal section in a target vessel.

Aneurysms are one of the most common pathologies of the human vascular system. Aneurysms are protuberances or bulges occurring in the vascular wall. The specific causes can be very different, but it can generally be said that the affected part of the vessel wall is weakened initially and afterwards widens due to the constant blood pressure acting on it.

In general, aneurysms may occur in all regions of the body and in all locations of the vessel system. Nevertheless, there are certain sites in the human body that are predestined for the formation of aneurysms because of their vascular anatomy alone. This includes, for example, all vascular branching locations, so-called bifurcations.

There are two aspects concerning the danger that an aneurysm poses to a patient's health. On the one hand, the aneurysm itself can lead to problems if it exerts pressure on other vessels or organs, for example. This may cause pain and/or result in an undersupply of other parts of the body and organs. For instance, if the brain is affected, more or less severe neurological deficits are the result.

On the other hand, a rupture of the aneurysm may take place, that is, aneurysms are also prone to tearing. This is particularly dangerous for the patient if the aneurysm is situated in the brain or on a large vessel that is carrying or conducting a great volume of blood. Brain hemorrhage may be caused in the event burst aneurysms occur in the brain, which may result in mild to most severe neurological damage depending on the size of the vessel and the severity of the bleeding, and in the worst case, such a brain hemorrhage may even lead to the death of the patient. If an aneurysm tears on a large vessel in the patient's body, fatal blood loss can occur within a very short time, for example in the event of ruptures of abdominal artery aneurysms or thoracic aneurysms.

Until a few years ago, many aneurysms required an open surgical treatment but, meanwhile, a wide range of alternative treatment options and medical devices is now available for the minimally invasive and intravascular treatment of aneurysms.

One of the preferred minimally invasive, intravascular aneurysm treatment options is the placement of stent grafts. A stent graft comprises a stent framework and a covering, which when combined results in a tubular implant. For the treatment of an aneurysm, such a stent graft bridges the area of the aneurysm by connecting the healthy portions of the vessel via the stent graft, with the blood in the area of the aneurysm then flowing through the stent graft. On the one hand, a rupture of the aneurysm is thus prevented and, on the other, the pressure that the aneurysm has exerted on other structures is largely eliminated as blood is no longer allowed to pass through the aneurysm.

The placement of such a stent graft in the form of a simple tubular element becomes particularly problematic when lateral branches leave the affected vessel in the area of the aneurysm. In this case, the implantation of a stent graft causes the lateral branches in this area to be also cut off from the blood supply, just like the aneurysm itself. Accordingly, the areas and/or organs to be perfused via the side branches are cut off from the blood supply.

In order not to cut off the side branches from the flow of blood, it is necessary to supply them via stent graft leads. In the state of the art, a large number of techniques are known that offer possible solutions. Today, it is primarily custom-made or modular implants that have established themselves, which are tailored to the needs of each individual patient. Such custom-made products and also modular systems are expensive. Manufacturing special custom-made products is time consuming, as they usually have to be made individually by hand. Modular systems, on the other hand, are quite frequently assembled by the surgeon in the patient in the course of the intervention.

For example, publication EP 2 749 251 B1 (Cook Medical Technologies LLC) discloses an extendable stent graft consisting of a base body and rings that is capable of being modularly adapted in a certain manner to the respective vessel anatomy. And EP 2 081 515 B1 (Cook Medical Technologies LLC) discloses a special window arrangement in stent grafts so as to be able to connect lateral branches to the implant as universally as possible. In addition, publication WO 2014/197743 A1 (Aortic Innovations Surena LLC) claims a variable stent graft system, the modular design of which allows the diverting lateral branches of the implant to be adapted to the vascular anatomy of the patient in predetermined longitudinal paths.

All these systems are associated with disadvantages. As a rule, implantation requires an experienced surgeon, in many cases even system-related training is necessary in order to construct the modularly designed implants correctly in the patient's body in the course of the intervention.

Moreover, an implantation of custom-made, i.e. tailored systems also presents the surgeon with major challenges. The anatomically accurate adaptation of the implant to the main branch and the accesses to the lateral branches requires the surgeon to fit the implant very precisely into the patient's anatomy. What appears to be quite simple in the rigid model is in practice a very difficult undertaking, because the vessels are not at all rigid and may change their position relative to each other.

The consequences of using such complex systems, whether they are completely assembled or of modular design, are a sometimes long and thus stressful intervention duration for the patient and the surgical team, and, what is more, an increasing probability of device failures.

Moreover, the state-of-the-art systems usually have to be completely implanted in the course of a single intervention. A step-by-step implantation, whether planned or as a reaction to the patient's condition, is ruled out in all probability, or at least not without risk, because only a completely implanted system will produce the desired result. Due to this, the surgeon can hardly react, for example, to a worsening condition of the patient during the intervention by postponing partial steps to a later date. Similarly, it is normally impossible from the beginning to perform planning of the intervention to take place over several days.

Also, the access possibilities of known systems are often limited as a result of their design configuration. Due to their complexity, these systems as a rule have quite large diameters even when in folded state and, consequently, need to be inserted only through correspondingly large introducer sheaths. Usually, this prevents the system to be introduced via the arm. Likewise, a retrograde access, for example to connect the lateral branches, is usually impossible with known systems for design-related reasons.

Another disadvantage of the prior-art systems is that they may develop a leak, a so-called endoleak, through migration (displacement of the prosthesis), texture damage or the progression of the disease in the upper and lower sealing segment. Relevant remedial action can be extremely sophisticated and as a rule can only be performed openly by surgery.

Another decisive disadvantage of the prior-art systems is that they need to be tailored to the specific situations. The prior-art systems, even if they are of partially modular design, must in most cases still be made by hand to suit the requirements of the specific case. Usually, this takes days or even weeks and in exceptional cases may require several months before they are available. More often than not, emergency care with such implants is therefore not possible, which may lead to the avoidable death of a patient within the waiting period for an appropriate implant.

It is therefore an objective of the present invention to provide a multilumen implant that is suitable for the treatment of a plurality of patients and a variety of clinical pictures due to its universal application and connection possibilities, without the need for pre-interventional tailoring or individualization. Such a system is also suitable for emergencies and can be stored in hospitals so as to be readily available.

Another objective of the present invention is the provision of a multilumen implant having an as small a diameter as possible in the folded state, which can be introduced accordingly via an introducer sheath of small diameter, so that aside from femoral accesses, in particular arm accesses can also be used as standard procedure.

It is moreover the objective of this invention to provide a multilumen implant that is compatible with customarily available accessories. In particular, it should be possible to use as many of the available prior-art covered stents and stent grafts as possible with a view to connecting the implant to the continuing vascular system. Similarly, stepwise interventions should also be made possible.

Still another objective of the invention is to provide a system that can be designed in an as simple as possible manner and is very easily implanted. This minimizes both the costs and failure rates of the system as well as the duration and risks of intervention.

It is also the task of the invention to provide an implant that is suitable for taking remedial action on prior-art systems in the event of a defect, by providing a seal that is completely independent of the original system and offering its own anchoring method, so that already placed prosthetic components, for example of an endograft, can remain in the body.

The implant proposed by the invention pursues an approach to attaining the objectives called for, which differs conceptually clearly from that of prior-art implants.

Prior-art implants attempt to reproduce the anatomy of the damaged vascular region, so to speak try to provide a lining of the region to be repaired. Accordingly and as described hereinbefore, these implants must be individually fabricated and implanted as accurately as possible. On the other hand, an implant according to the present invention is to be viewed as a kind of distributor insert, in principle, the lumen of which can be individually connected to the vessels to be treated with the aid of covered stents.

This objective is achieved by a multilumen implant featuring the characteristics described in claim 1. Advantageous embodiments in each case are the subject of the dependent claims. It is to be noted that any features and characteristics individually included in the claims may also be combined with each other in an optional and technologically sensible manner so that they reveal further implementations or methods of the invention.

In a first embodiment of the invention proposed, the implant consists of a substantially tubular element and at least one stent used for the fixation of the tubular element in a vessel.

The tubular element is structured to form a proximal and a distal section, with the distal section branching into at least two lumina. In the present application, the term distal always denotes the part of a structure that points in the direction of the blood flow, so that, correspondingly, the term proximal denotes the part that faces against the direction of the blood flow.

The tubular element can be imagined as and compares to a kind of glove. In such a comparison, the proximal section of the tubular element corresponds substantially to the part of the glove surrounding the palm of the hand while the distal section of the tubular element substantially corresponds to the fingers of the glove, with the distal branches of the implant that correspond to the fingers ending openly or being openable at their ends.

In a preferred embodiment, the proximal lumen branches distally into five lumens, one main lumen and four secondary lumens, but other subdivisions are easily conceivable and can be realized without difficulty. The implant proposed by the invention is in no way limited to embodiments which resemble the proportions, dimensions or other characteristics of a finger glove.

The tubular element can be secured by means of at least one stent on the inside or outside of the proximal section of the tubular element upstream of the aneurysm in the target vessel. The tubular element may be attached to the stent by further measures, for example by clamping, welding, bonding, sewing or other known techniques. Especially preferred is a clamp-like connection, as disclosed in publication WO 2012/084202 A2. It is also conceivable to provide embodiments, in which the proximal section of the tubular element is located between two stents and, if necessary, is additionally attached, as described hereinbefore, to one or both stents.

In this context, it is conceivable to make use of embodiments that provide for the stent to not exclusively be located in the proximal section of the tubular element, but projects into the distal region or even beyond the end of the distal region. In this way, for example, a more or less long first portion of the proximal section of the tubular element may not be covered by the stent and, accordingly, this first portion may then be folded inwards or outwards around the proximal end of the stent.

A preferred embodiment, however, is one in which the proximal section of the tubular element is at least partially folded around the distal section of the tubular element. In a particularly preferred embodiment, the stent for the fixation of the tubular element is then located in the folding or foldover created between the original outer sides of the proximal and distal sections of the tubular element.

Another preferred embodiment within the meaning of what has been elucidated above provides for the proximal section of the tubular element to be folded over upon the distal section, with the length of the folded over proximal section exceeding the length of the stent located in the folding so created. In this manner, the part of the proximal section that protrudes distally beyond the stent can be folded inwards around the distal end of the stent, so that the stent is then wrapped at both ends by the proximal section of the tubular element.

The distal section of the tubular element branches into at least two lumens, whereby the number of lumens is arbitrary and the number of branches may be selected, for example, depending on the number of vessels to be perfused. However, preferred are embodiments in which five branches are arranged.

Particularly preferred are embodiments comprising of one main lumen with a larger diameter and four secondary lumens having a smaller diameter. Nevertheless, the diameters are basically arbitrary and can be selected so as to be suitable for the intended use of the implant. When using the implant in the thoracic and abdominal area, diameters of the proximal section may range between 5 and 45 mm, preferably between 20 and 42 mm, possible diameters for the main lumen range between 3 and 30 mm, preferably between 12 and 25 mm, and for the secondary lumens diameters between 2 and 12 mm, preferably between 4 and 10 mm, may be used. When it is intended to use the implant in the cerebral area, diameters of the proximal section may range between 2 and 15 mm, preferably between 2 and 8 mm, possible diameters for the main lumen range between 1 and 5 mm, preferably between 2 and 4 mm, and for the secondary lumens diameters between 1 and 4 mm, preferably between 2 and 3 mm, may be used. In the event the implant is to be applied in the coronary area, diameters of the proximal section may range between 2 and 8 mm, preferably between 4 and 6 mm, possible diameters for the main lumen range between 2 and 6 mm, preferably between 3 and 5 mm, and for the secondary lumens diameters between 2 and 5 mm, preferably between 2 and 3 mm, may be used.

Aside from the embodiments referred to above, it is also conceivable that embodiments may be provided with a total of more or less than five lumens, and, moreover, that the embodiments may have more than one main lumen and more or less than four secondary lumens.

If one thinks of a cross-section through an area of the implant after branching, it is preferred to make use of embodiments having an eccentric distribution of the lumens, in which case the branching with the largest lumen is located on one side and one or more branches of smaller lumens are arranged on the other side in the cross-sectional view. However, the distribution of the branches in the distal section of the tubular element is not predetermined, and it is also conceivable that embodiments can be used in which, for example, one branch is located in the central area and other branches are uniformly or unevenly distributed around the central lumen.

In a preferred embodiment, the individual branches have the same length, but other embodiments that provide for the branches to be of different lengths are also conceivable. On the whole, it is preferred if the branches terminate distally approximately with the stent for the fixation of the implant. It is conceivable, however, that, distally, the stent also reaches over the branches or that the branches protrude distally from the stent framework.

The branches of the implant are connected to the vessels located distally to the implant via covered stents, so-called stent grafts, resulting in bridging the aneurysm area in this manner thus preventing the flow of blood into the aneurysm and relieving pressure on the aneurysm. At the same time, the distally located vessels are purposefully supplied with blood via the stents.

For better fixation of the stents that connect the distal branches of the tubular element to the vessels each to be supplied with blood, the distal branches in a preferred embodiment may taper conically towards their end entirely or over a certain length of a respective branch.

Further measures to secure the stents in the distal branches are conceivable in the form of ring-shaped or other reinforcements or stiffeners, especially in the distal areas.

On the one hand, this ensures the firm fit of the stent graft and due to this reinforcement also reduces the risk of tearing of the distal branches during the implantation of the stent grafts.

The branches in the distal section preferably run freely from each other, but embodiments are also conceivable that provide for some or all of the branches to be bonded together, if thought expedient also in groups. The branches may also be attached—additionally or alternatively—to the stent serving to secure the implant in place or to the folded-around proximal section of the tubular element.

As materials for the tubular element any physiologically compatible material known to the state of the art can be employed, primarily ePTFE, said materials may also be processed by electrospinning.

For the stent or stents, all materials known in the state of the art can be used, which guarantee a permanent fixation of the tubular element and are not resorbable. Suitable for this purpose are both alloys that enable a balloon expansion to be brought about and shape memory materials such as nickel-titanium alloys.

Typically, the implant proposed by the present invention is placed at the proximal end of the aneurysm in the still intact vascular section. In this case, the implant fulfils the function of a distribution disk or element that allows the blood to flow exclusively through the lumina of the distal branches. With a view to bridging the region of the aneurysm, the distal branches of the tubular element are connected via covered stents to the vessels located distally to the implant.

This technique makes it possible to also carry out the intervention step by step due to the fact that the placement of the implant initially does not prevent the flow of blood to the vessels situated distally to the implant. In this manner, the implant itself can be placed in position in a first intervention for example, with the vessels being connected subsequently in one or several further interventions.

What is more, a retrograde access that is difficult or even impossible to realize with prior-art implants can be achieved in order to connect the vessels and branches of the implant with each other.

As a result of its universal adaptability, the multilumen implant the invention proposes also enables the repair of already placed systems which have developed a leak, a so-called endoleak, due to migration (displacement of the prosthesis), texture damage or the progression of the disease in the upper and lower sealing segment. The already implanted prosthetic parts may remain in the body, because the multilumen implant offers a completely independent sealing effect and its own anchorage system.

However, a variety of other advantages are offered by an implant according to the invention. They also relate to manufacturing costs and thus to the costs of the health system, patient safety, improved scheduling, availability, product safety and also the safety of relevant interventions.

Due to its universal applicability, the implant can be produced in larger quantities at correspondingly lower unit costs due to its standardization to five distally arranged lumens and, therefore, is significantly more cost-effective than individualized implants.

Since the implant is universally useable because of its flexible connection options, it can be kept in stock in the clinic and thus also employed in acute emergencies. An individual tailored production sometimes associated with long waiting times is thus rendered unnecessary.

The implant is easy to implant, it does not have to be prepared beforehand nor assembled in the patient's vascular system. Basically, implantation is carried out in the same way as the insertion of a normal stent. For the connection of the branches to the vessels no special knowledge is required either, it corresponds to the routine placement of stent grafts.

In comparison with prior-art implants, the straightforwardness of the inventive implant also makes it lesser susceptible to device failures which may be experienced in the course of the intervention or be the result of previous fabrication, processing and preparation activities.

Last but not least, it is to be assumed that the safety aspects of the actual intervention will improve, since due to the simplicity of the intervention process—the complicated connection of the vessels and the assembly of the implant in the patient are eliminated—the intervention time and thus automatically the risk of surgery-related complications will be reduced.

The invention as well as the technical environment are described hereunder in sufficient detail on the basis of the figures. It is to be noted that the figures show an especially preferred embodiment variant of the invention. However, the invention shall not be deemed as being limited to the embodiment variant shown. To the extent it is technically expedient, the invention comprises, in particular, any optional combinations of the technical features that are stated in the claims and in the description and pertinent figures as being relevant to the invention.

Elucidation of the invention is provided by the following figures where.

Figure 1:
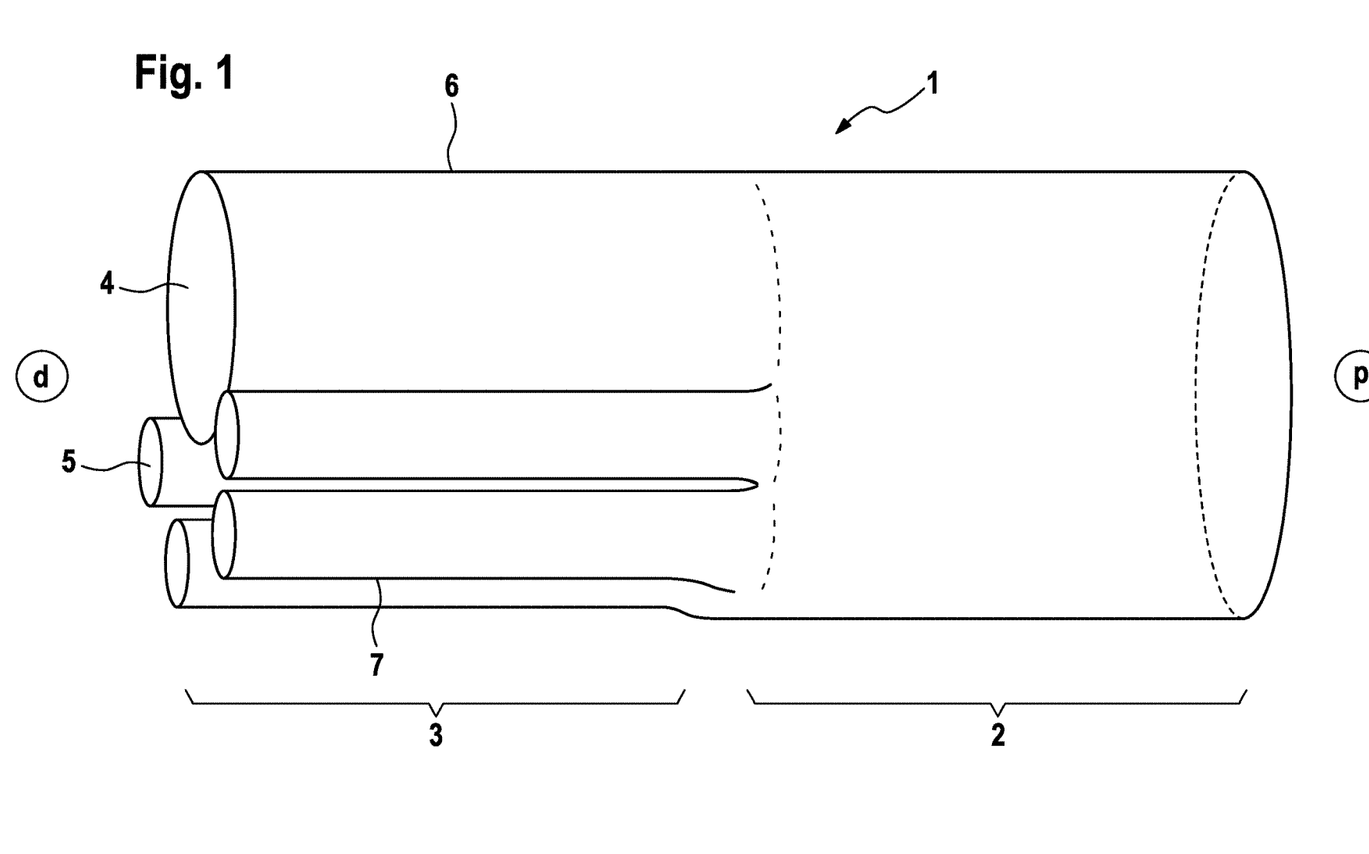
FIG. 1 shows a schematic representation of the tubular element.

FIG. 1 shows a schematic representation of the tubular element 1 of an implant in accordance with the invention, said implant being divided into a proximal section 2 and a distal section 3. The proximal (p) single-lumen tubular element 1 branches distally (d) into at least two lumens 4, 5, with a preferred embodiment comprising one main lumen 4 and four secondary lumens 5, or correspondingly one large branch 6 and four smaller branches 7.

The relative proportions shown in this schematic representation have been selected purely with a view to rendering the individual parts to be easily recognizable. Accordingly, the ratio of proximal section 2 to the distal section 3 as well as the ratios of the individual distal lumens 4 and 5 or the lengths of the branches 6 and 7 may differ from what is shown in the figure.

Figure 2:
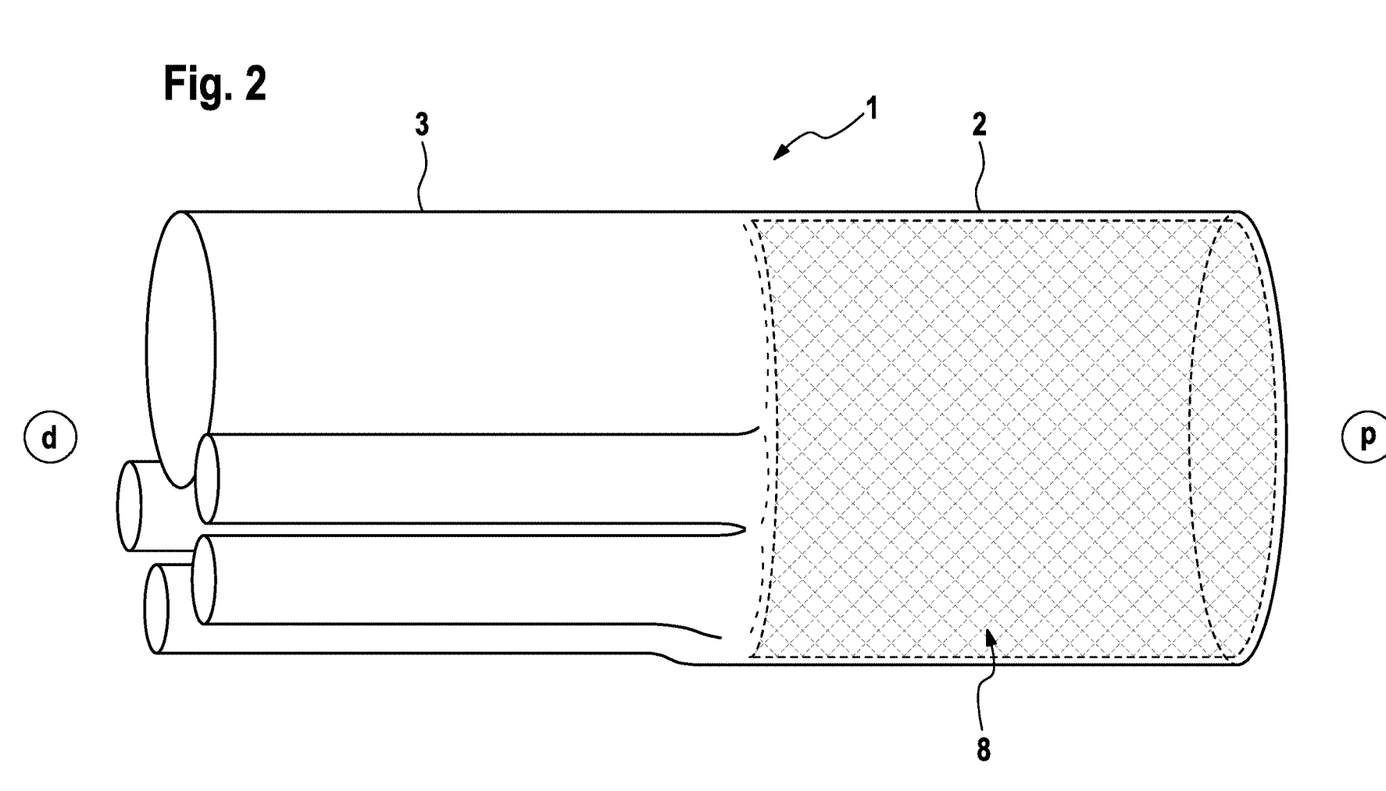
FIG. 2 is a schematic representation of a first embodiment of the implant proposed by the invention.

FIG. 2 illustrates the tubular element 1 shown in FIG. 1, with a stent 8 for securing or fixation of the tubular element 1 now being located in a vessel inside the proximal section 2. In this embodiment, the stent 8 reaches up to the distal section 3. If considered expedient, the proximal end of the tubular element 1 may project beyond the stent 8 and be folded inwards over the proximal end of the stent into the lumen of the proximal section 2.

Figure 3A:
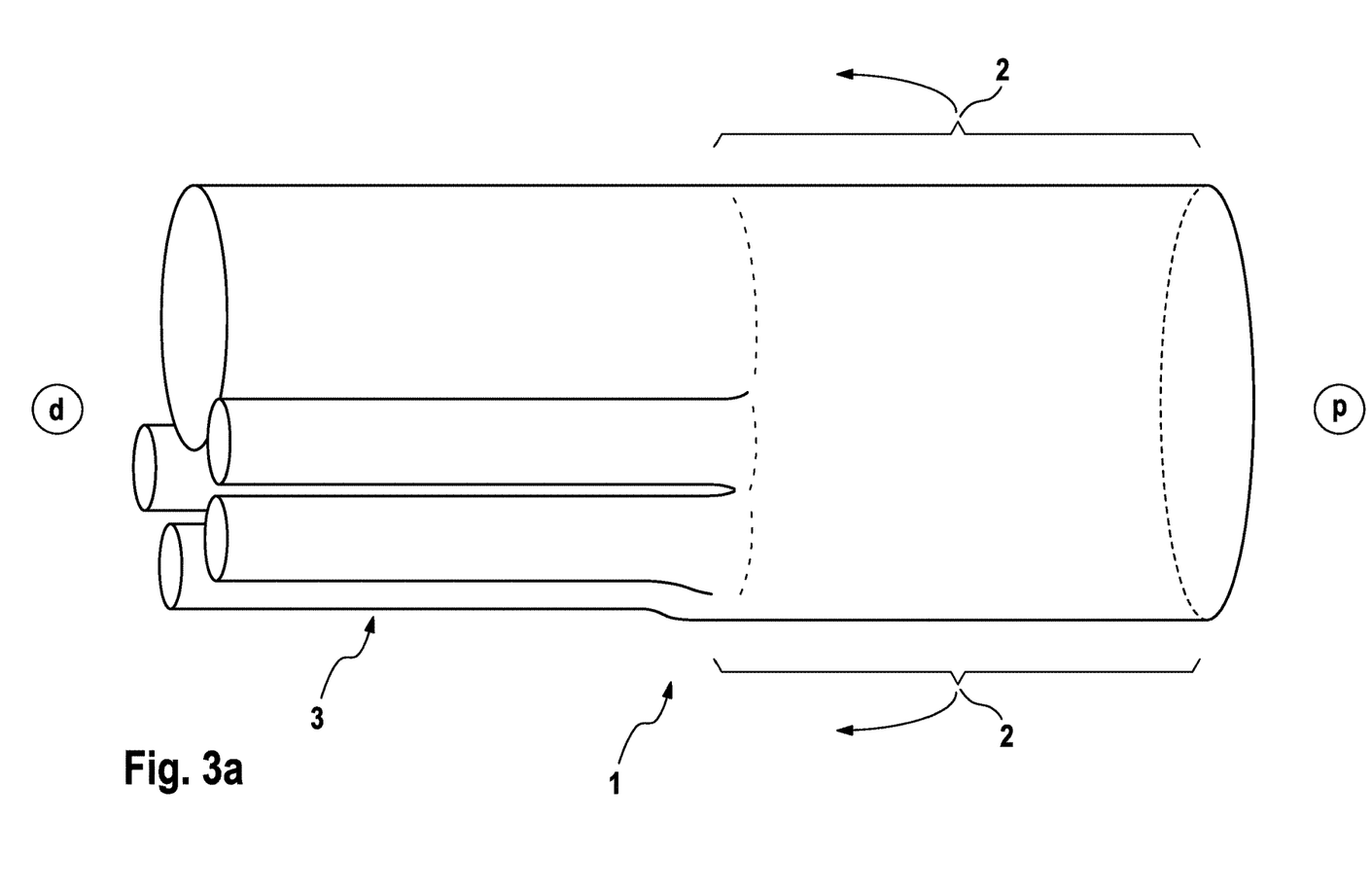
FIG. 3a-b illustrate a schematic representation of the folding of the proximal onto the distal section for a better understanding of a second embodiment of the inventive implant.
Figure 3B:
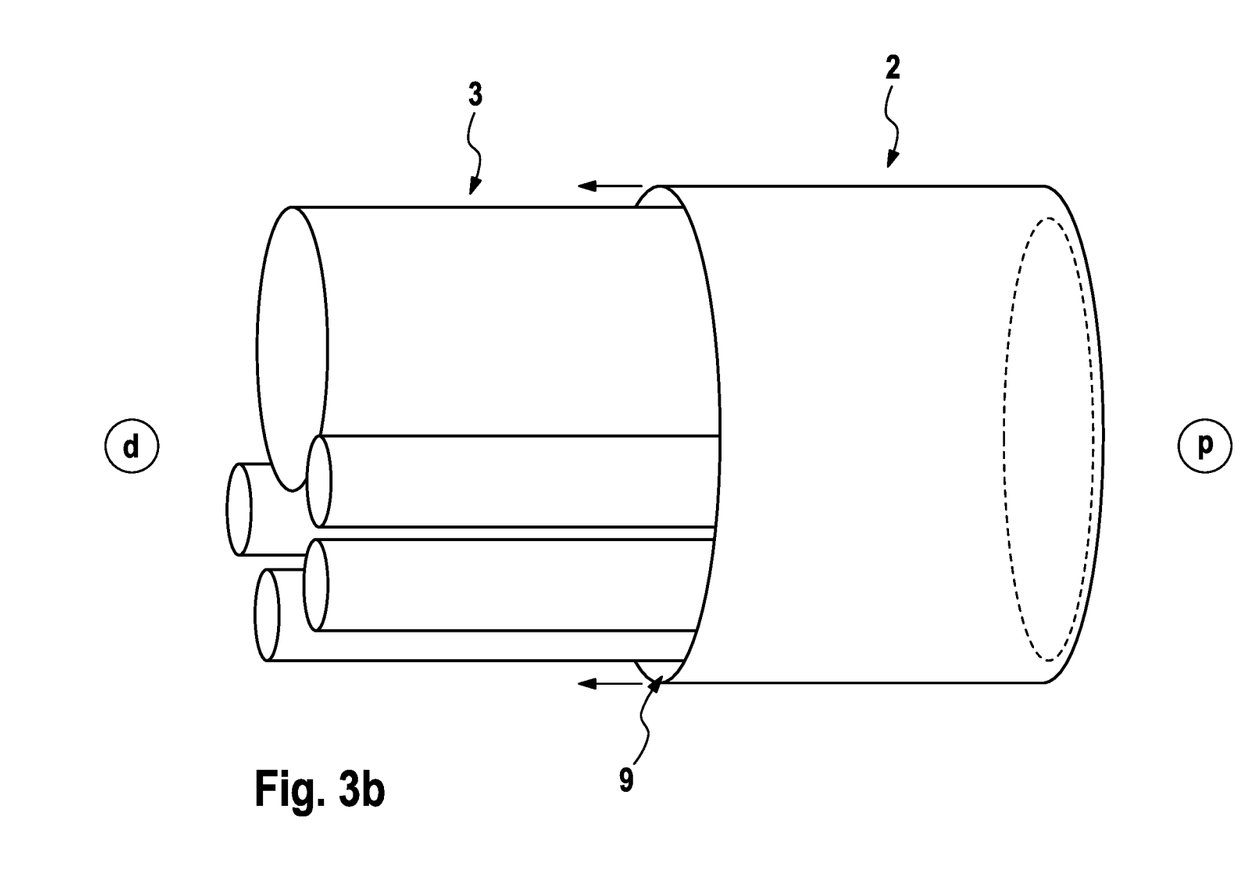

FIGS. 3a and 3b indicate the arrangement of the proximal section 2 of the tubular element 1 in a first preferred configuration. In this case, the proximal section 2 is folded over onto the distal section 3, so that the distal section 3 is finally at least partially encased by the proximal section 2.

Figure 4A:
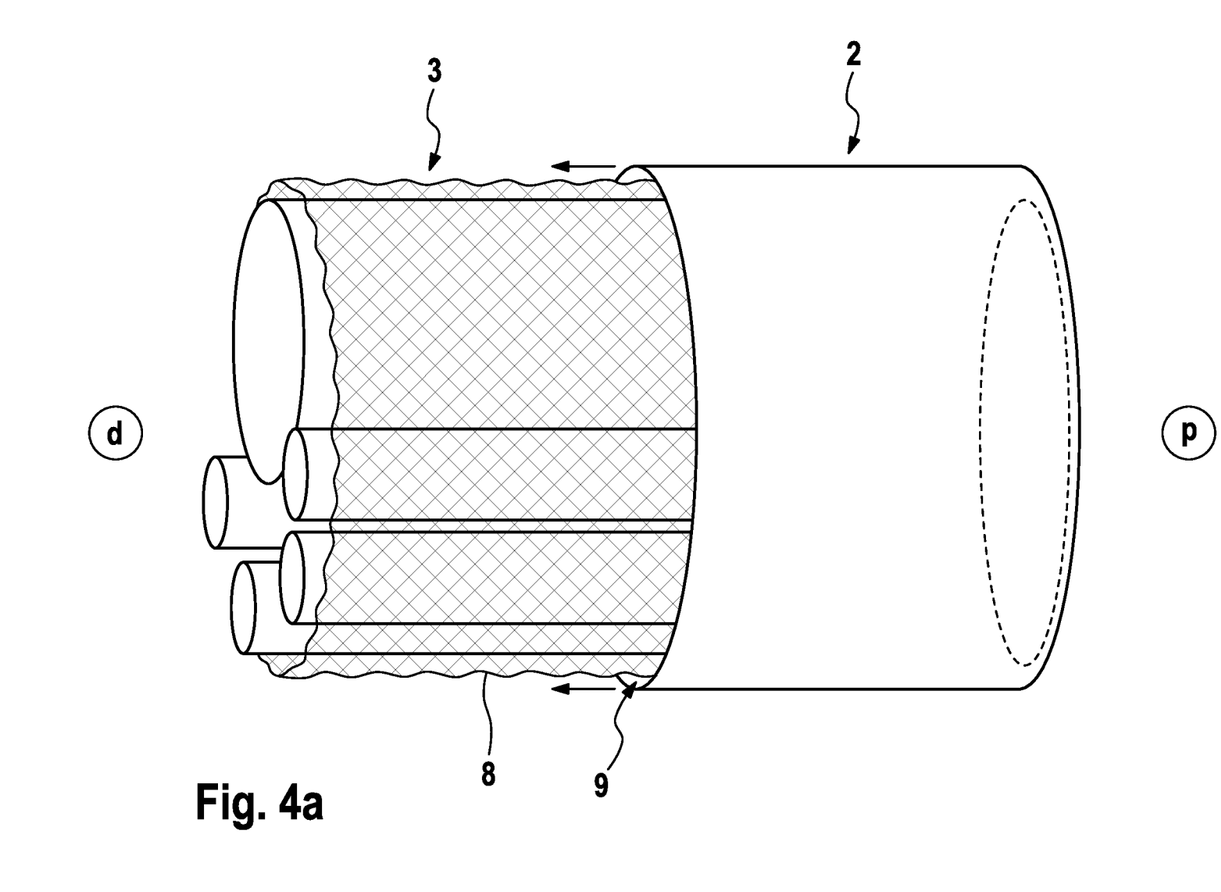
FIG. 4 is a schematic representation of a further folding of the proximal onto the distal section and the position of the stent for a better understanding of a second embodiment of the inventive implant.
Figure 4B:
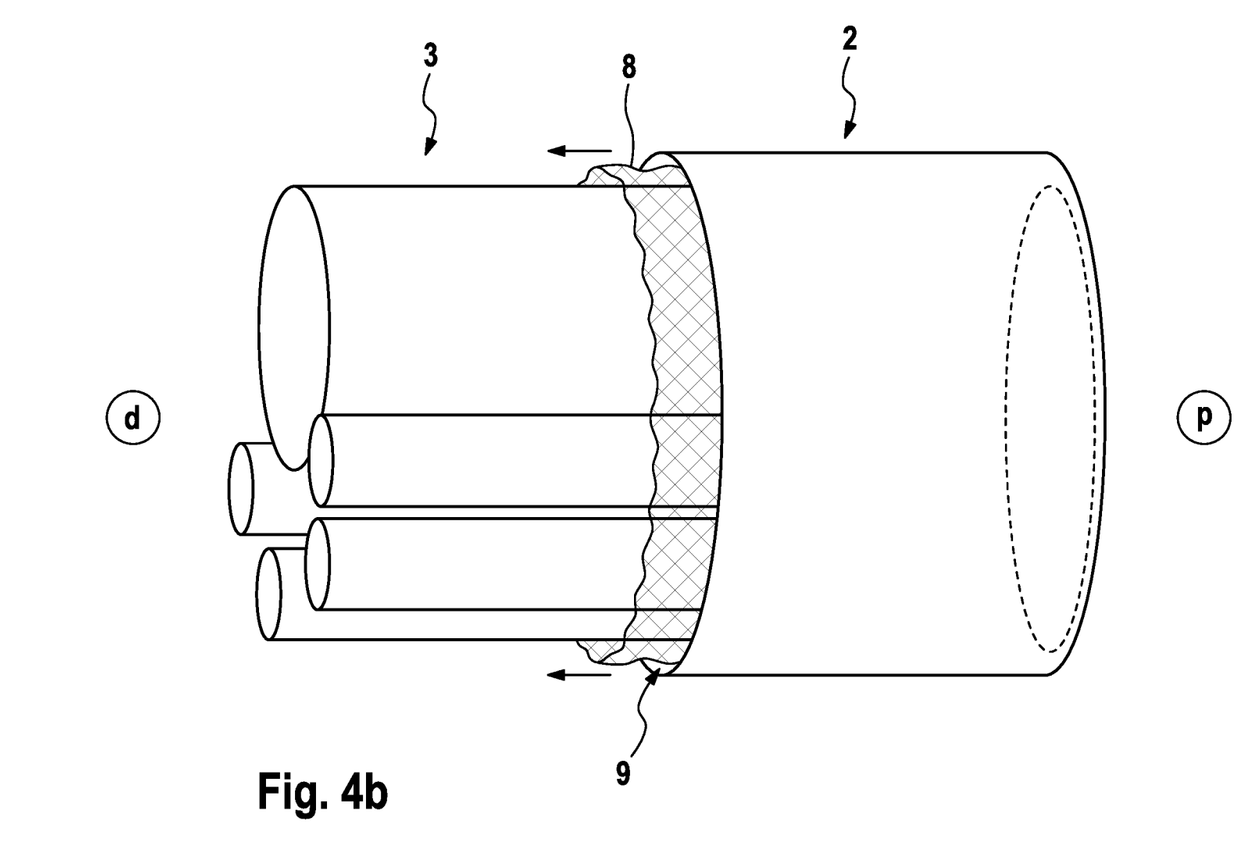

FIGS. 4a and 4b illustrate two variants of a first preferred embodiment that are based on the folding of the proximal section 2 as can be seen in FIGS. 3a and 3b. The variants 4a and 4b shown here differ in the length of the stent 8, which is located in the folding 9 formed by the folded over components, but protrudes distally (d) to different extents from the folding and, accordingly, protrudes over the distal section 3 to a greater extent 4a or lesser extent 4b.

Figure 5:
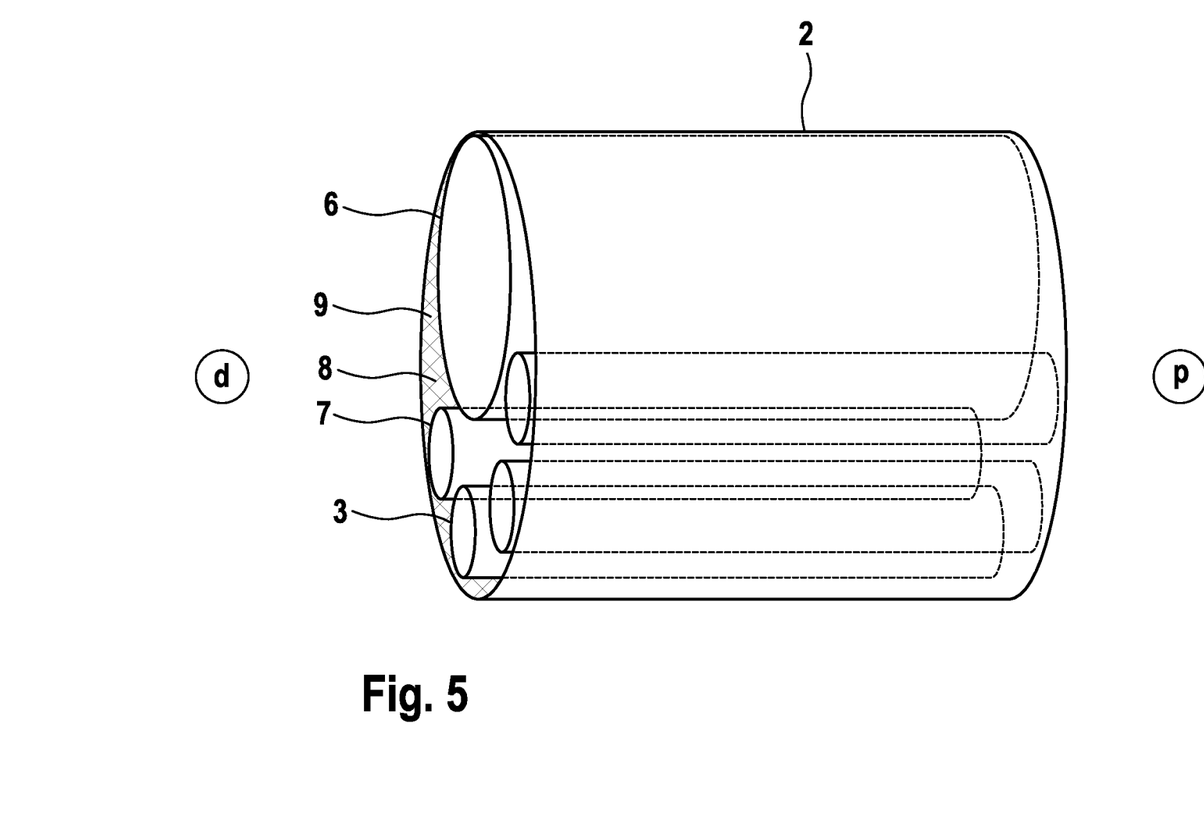
FIG. 5 is a schematic representation of a second embodiment of the implant proposed by the invention.

FIG. 5 depicts a preferred embodiment which is based on the folded over proximal section 2 as shown in FIGS. 3a and 3b. The proximal section 2 is folded over distally (d) up to the end of the branches 6, 7. A stent 8 is contained in the folding 9 so created.

Figure 6:
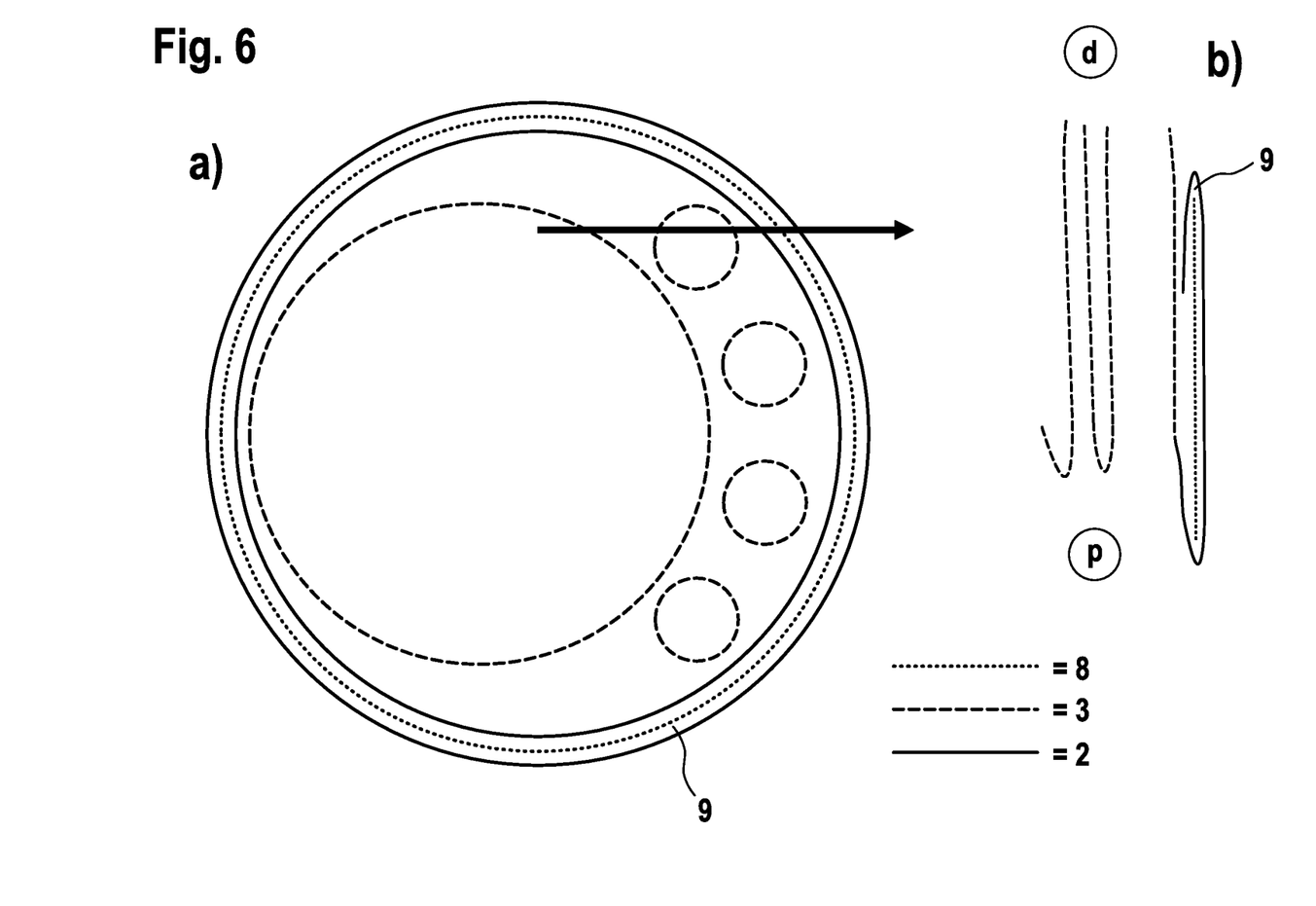
FIG. 6a-b show a transverse a) and a longitudinal section b) through a second embodiment of the implant according to the invention.

FIG. 6 shows a cross section 6a and a longitudinal section 6b through the preferred embodiment of the implant illustrated in FIG. 5. The dotted line identifies the stent 8, the dashed line the distal section 3 and the continuous line the proximal section 2 of the tubular element 1.

Figure 7:
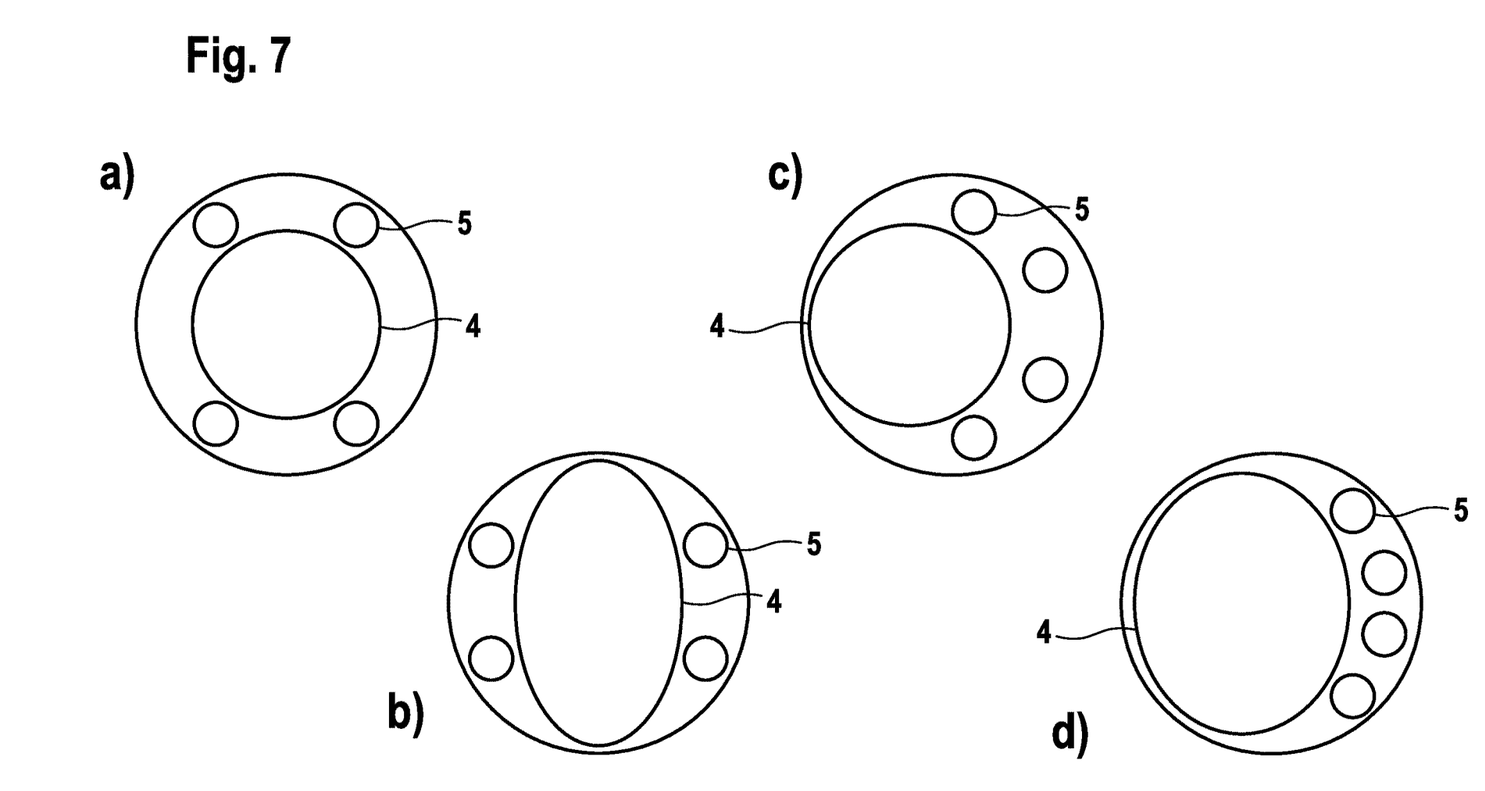
FIG. 7a-d show a schematic representation of possible distribution options of the distal lumina.

FIG. 7 is a schematic representation of cross sections through the implant, with different distributions and arrangements of the distal lumens 4, 5 being shown. The main lumen 4 may be arranged centrally (a, b) or eccentrically (c, d). The secondary lumens 5 can be arranged around the main lumen 4 (a, b) or on one side of it (c, d). In the cross-sectional view, the main lumen 4 can be of round shape (a, c) or oval (b, d). Conceivable as well are embodiments in which the secondary lumens 5 also have an oval shape. A preferred embodiment is illustrated in FIG. 7c.

Figure 8:
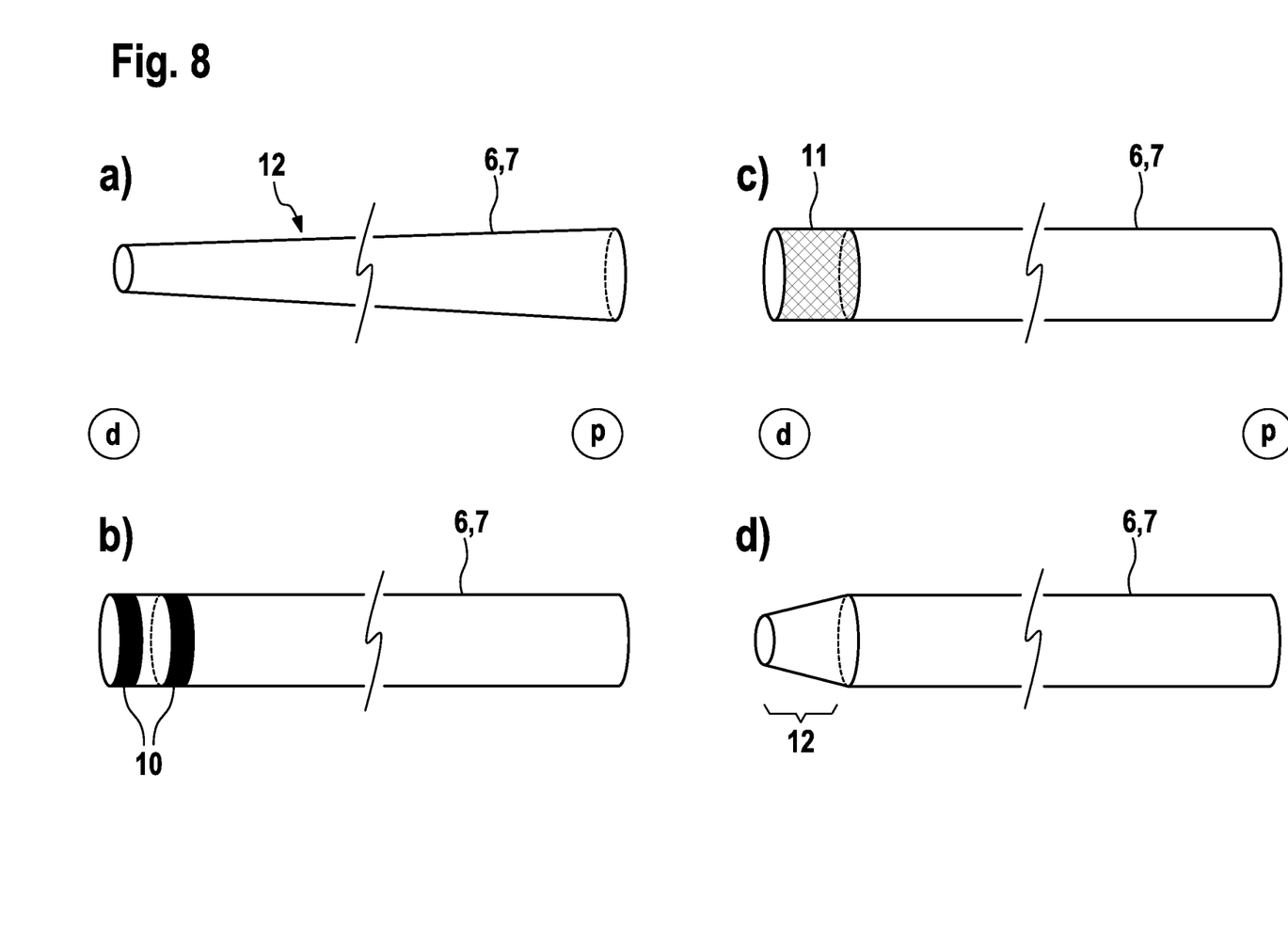
FIG. 8a-d show possible configurations of the distal ends of the branches for better fixation of the stents passing on the blood.

FIG. 8 shows various design options for the distal ends d of the distal branches 6, 7 for better fixation of the stents, which connect the distal branches 6, 7 with the respective vessels to be perfused. For this purpose and in a preferred embodiment, the distal branches may be tapered conically towards their end 12 entirely (a) or at the distal tip (d), at the tip they may have annular reinforcements 10 or a distally entirely reinforced structure 11 (c).

LIST OF REFERENCE NUMERALS

1 Tubular element
2 Proximal section
3 Distal section
4 Main lumen
5 Secondary lumen
6 Main branch
7 Secondary branch
8 Stent
9 Folding
10 Annular reinforcement
11 Annular reinforcement
12 Taper
p proximal
d distal

The invention claimed is:
1. Multilumen implant for the application in human and animal vascular systems/bodies, comprising a substantially tubular element (1) that divides into a proximal (2) and a distal section (3), and at least one stent (8) for the fixation of the proximal section (2) in a target vessel wherein the tubular element (1) is designed to branch in the distal section (3) into at least two branches (6, 7) with respective lumens (4, 5); and the proximal section (2) of the tubular element (1) is at least partially folded over upon the distal section (3) and the stent (8) is at least partially arranged inside a folding (9), characterized in that the length of the folded proximal section (2) of the tubular element (1) corresponds to at least the length of the stent (8) and wherein the branches (6, 7) together are at least partially arranged inside the stent (8).

2. Multilumen implant according to claim 1, characterized in that the tubular element (1) branches in the distal section (3) into a main lumen (4) and a plurality of secondary lumens (5).

3. Multilumen implant according to claim 2, characterized in that the secondary lumens (5) have a smaller caliber than the main lumen (4).

4. Multilumen implant according to claim 1, characterized in that the stent (8) is inside of the proximal section (2) of the tubular element (1).

5. Multilumen implant according to claim 1, characterized in that the stent (8) is contacting the surface of the proximal section (2) that was outside prior to folding of the tubular element (1), wherein the proximal section of the tubular element (1) has a first part that is outwardly guided distally at least partially around the proximal part of the stent (8).

6. Multilumen implant according to claim 1, characterized in that the proximal section (2) of the tubular element (1) is longer than the stent (8) and in that the portion of the proximal section (2) projecting distally (d) beyond the stent (8) is folded inwardly over the stent (8).

7. Multilumen implant according to claim 1, characterized in that the lumens (4, 5) of the distal section (3) of the tubular element (1) taper in distal direction (d) (12).

8. Multilumen implant according to claim 1, characterized in that the branches (6, 7) have distally annular reinforcements (10, 11).

9. Multilumen implant according to claim 1, characterized in that the tubular element (1) is secured to the stent (8) by means of clamping, bonding/gluing, sewing or welding.

10. Multilumen implant according to claim 1, characterized in that the tubular element (1) consists of ePTFE.

11. Multilumen implant according to claim 10, characterized in that the tubular element (1) made of ePTFE is produced by electrospinning.

12. Multilumen implant according to claim 1, characterized in that the stent (8) is a self-expanding stent.

13. Multilumen implant according to claim 1, characterized in that the stent (8) is a balloon-expanding stent.

14. Kit comprising an implant according to claim 1 and a balloon catheter and/or a catheter for its implantation.

15. Kit according to claim 14, moreover comprising stent grafts sufficient in number for the purpose of connecting respective distal branches (6, 7) of the implant to the distal vessels.

* * * * *